United States Patent [19]

Hubbard et al.

[11] 4,020,165
[45] Apr. 26, 1977

[54] CONTROL OF ACARIDS USING CERTAIN BENZOTHIAZOLES OR BENZOTHIAZOLINES

[75] Inventors: Winchester L. Hubbard, Woodbridge; Robert E. Grahame, Jr., Cheshire; Rupert A. Covey, Bethany; Elmar H. Jancis, Naugatuck, all of Conn.

[73] Assignee: Uniroyal Inc., New York, N.Y.

[22] Filed: June 4, 1976

[21] Appl. No.: 693,054

Related U.S. Application Data

[62] Division of Ser. No. 606,376, Aug. 20, 1975, Pat. No. 3,974,287, which is a division of Ser. No. 543,717, Jan. 24, 1975, Pat. No. 3,928,617, which is a division of Ser. No. 420,749, Nov. 30, 1973, Pat. No. 3,876,791.

[52] U.S. Cl. ............................................. 424/270
[51] Int. Cl.² ........................................ A01N 9/22
[58] Field of Search ................................... 424/270

[56] References Cited
UNITED STATES PATENTS

| 3,095,422 | 6/1963 | Duennenberger et al. | 424/270 |
| 3,647,812 | 3/1972 | Smith | 260/304 |
| 3,669,979 | 6/1972 | Freyormuth | 260/304 |

*Primary Examiner*—Allen J. Robinson
*Attorney, Agent, or Firm*—James J. Long

[57] ABSTRACT

Compounds having either of the structures

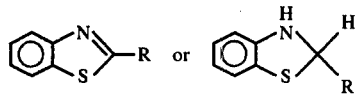

have strong acaricidal activity, in which R is a phenyl or naphthyl group, or phenyl with certain designated substitution. Thus, mites may be controlled on such crops as cotton by applying such compounds as 2-(1-naphthyl)benzothiazoline or 2-(5-t-butyl-2-hydroxyphenyl)-benzothiazole.

6 Claims, No Drawings

CONTROL OF ACARIDS USING CERTAIN BENZOTHIAZOLES OR BENZOTHIAZOLINES

This is a division of application Ser. No. 606,376, now U.S. Pat. No. 3,974,287 issued Aug. 10, 1976, filed Aug. 20, 1975, which is in turn a division of application Ser. No. 543,717, filed Jan. 24, 1975, now U.S. Pat. No. 3,928,617, issued Dec. 23, 1975, the later being in turn a division of application Ser. No. 420,749, filed Nov. 30, 1973, now U.S. Pat. No. 3,876,791, issued Apr. 8, 1975.

This invention relates to a method of controlling acarids, using certain benzothiazoles or benzothiazolines and to an acaricidal composition useful in such method.

Acarids which are controlled by the method of the invention include plant-feeding mites and mites and ticks which afflict man and animals.

Plant-feeding mites produce enormous losses to agricultural crops in a world plagued by constant shortages of food. Crops such as alfalfa, apples, corn, cotton, grapes, oranges, potatoes, sorghum, peanuts and many others may be completely devastated by these tiny pests.

In addition, various species have become so specialized in structure and habit that they must subsist on the bodies of man and animals. Few domesticated or wild animals are immune to their attack. Mites are expert at tormenting their host. There is probably no creature in existence which can cause more torment for its size than a "chigger" can by burrowing beneath the skin of man.

Other species such as itch and mange mites cause serious skin diseases in animals such as dogs, cats, rabbits, horses, cattle and pigs.

Ticks and some species of mites suck the blood of man and animals. Besides the irritation involved, a multitude of animal diseases may be transmitted by this method of food procurrement. Dread diseases such as Rocky Mountain spotted fever, relapsing fever and tularemia are transmitted by the bites of ticks.

During the last 30 years, numerous chemicals have been utilized in protecting both man and man's food and fiber against injury from mites and ticks. There is a continuing need for novel, effective and safe chemicals to accomplish this task.

In accordance with the invention it has now been found that certain benzothiazoles and benzothiazolines are highly effective acaricides. The benzothiazoles and benzothiazolines employed as acaricides in the method of the invention may be represented by the general formulas:

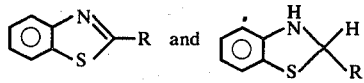

in which R is phenyl, naphthyl, or phenyl substituted with alkyl having 1 to 10 carbon atoms, cycloalkyl having 5 to 10 carbon atoms, halogen, hydroxyl, alkoxy having 1 to 14 carbon atoms, carbalkoxyalkoxy having 3 to 14 carbon atoms, cycloalkylalkoxy having 6 to 10 carbon atoms, cycloalkoxy having 5 to 7 carbon atoms, or acyloxy having 1 to 8 carbon atoms, or phenyl substituted with two alkyl, halogen or alkoxy substitutents as previously defined, or combinations of hydroxyl and alkyl, (as previously defined) or hydroxyl and halogen.

Examples of R are phenyl, 1-naphthyl, 2-naphthyl and phenyl substituted with the following: methyl, ethyl, n-propyl, isopropyl, n-butyl, 2-butyl, isobutyl, t-butyl, n-amyl, 2-amyl, t-amyl, hexyl, heptyl, n-octyl, t-octyl, nonyl, decyl, cyclopentyl, cyclohexyl, chloro, bromo, hydroxy, methoxy, ethoxy, n-propoxy, isopropoxy, n-butoxy, 2-butoxy, isobutoxy, t-butoxy, n-amyloxy, sec.-amyloxy, t-amyloxy, hexoxy, heptoxy, n-octyloxy, 2-octyloxy, nonyloxy, decoxy, undecoxy, dodecoxy, tridecoxy, tetradecoxy, carbomethoxymethoxy, carbomethoxyethoxy, carbethoxymethoxy, carbethoxypropoxy, carbethoxybutoxy, carbethoxypentoxy, carbopropoxymethoxy, carbopropoxypentoxy, carbocyclohexoxypropoxy, acetoxy, propionyloxy, butyryloxy, cyclopentoxy, cyclohexoxy, cycloheptoxy, cyclopropylmethoxy, cyclopentylmethoxy, cyclohexylmethoxy, cyclohexylethoxy, cyclohexylbutoxy, cycloheptylmethoxy. Phenyl groups substituted with a hydroxyl group may be additionally substituted with an alkyl or a halo group as indicated above. The phenyl group may also be substituted with two alkyl groups, two halo groups or two alkoxy groups.

Preferred compounds employed in the invention include those in which R is a phenyl or naphthyl group or a phenyl grup substituted with one of the following: alkyl (1 to 8 carbons), chloro, bromo, o-hydroxy, alkoxy (1 to 10 carbons), carbethoxyalkoxy (4 to 13 carbons), cycloalkoxy (5 to 6 carbons), cyclopentylmethoxy, or cyclohexylmethoxy, or substituted twice as follows: dimethyl, dichloro, dibromo, dimethoxy, diethoxy, hydroxyalkyl (1 to 5 carbon atoms), hydroxychloro or hydroxybromo. Preferred compounds may include two R' substituents on the phenyl ring where R is methyl, chloro, bromo, alkoxy (1 or 2 carbons) and combinations of hydroxy and alkyl (1 to 5 carbons) or hydroxy and halo (chloro or bromo).

The most preferred compounds are those in which R is naphthyl group, or a phenyl group substituted with one of the following: alkyl (1 to 6 carbons), chloro, bromo, o-alkoxy (3 to 8 carbons), o-carbethoxyalkoxy (6 to 11 carbons), o-cyclopentoxy, o-cyclohexoxy, o-cyclohexylmethoxy, or substituted twice as follows: dimethoxy, hydroxy-alkyl (1 to 5 carbons), hydroxybromo.

The chemicals employed as acaricides in the invention may be prepared by procedures well known and described in the literature, such as U.S. Pat. Nos. 3,669,979, Freyermuth, June 13, 1972, 3,647,812, Smith, March 7, 1972, 3,095,422, Duennenberger, et al., June 25, 1963, and by P. J. Palmer, et al., J. Medicinal Chem, 14, 248 (1971). The first two patents involve preparation of benzothiazoles by reacting an o-aminothiophenol with an aromatic acid in the presence of phosphorus trichloride. The third patent illustrates the preparation of benzothiazoles by combining the same reagents in the presence of a catalytic amount of boric acid. The fourth reference shows typical methods for the preparation of benzothiazolines which involve condensing the aminothiophenol with an aromatic aldehyde in the presence of absence of a solvent. The benzothiazoles employed in the invention are stable materials with characteristic melting points. The benzothiazolines, while usually isolated as pure materials with characteristic melting points, frequently can be oxidized to the corresponding benzothiazoles. Sometimes this oxidation can occur by exposure of a thin film of the chemical to air for several days. Tables I and II list typical chemicals useful in the invention with melting points and analytical data.

Typical experimental procedures for preparing the chemicals are illustrated as follows:

Preparation of 2-(2-Hydroxy-5-bromophenyl)benzothiazole

2-Aminothiophenol (12.5 g, 0.1 mole) was dissolved in 30 ml. of pyridine and 20.1 g (0.1 mole) of 5-bromosalicylaldehyde was added dropwise during 15 minutes. The solution was warmed on a steam bath for 2 hours and then a stream of air was bubbled through the mixture while heating for another hour. The mixture was poured into 300 ml. of 2 N HCl which was then stirred until crystals formed. The product was removed by filtration, washed with water and recrystallized from ethanol, mp. 164°–165°. Yield, 8.0 g. (26%).

Anal. Calcd. for $C_{13}H_8BrNOS$: C, 51.00; H, 2.63; N, 4.58. Found: C, 51.02; H, 2.59; N, 4.97.

Preparation of 2-(4-Chlorophenyl)benzothiazoline

2-Aminothiophenol (12.5 g, 0.1 mole) and 14.1 g (0.1 mole) p-chlorobenzaldehyde were combined in an Erlenmeyer flask at room temperature. The aldehyde dissolved in the mixture which became cloudy after a few minutes. Heat was evolved and the mixture gradually solidified. The product was recrystallized from ethanol yielding 18.0 g (73%) pale yellow crystals, mp. 85°–87°.

Anal. Calcd. for $C_{13}H_{10}ClNS$: C, 63.11; H, 4.08; N, 5.66. Found: C, 62.78; H, 4.01; N, 5.65.

Preparation of 2-(2,5-Dimethoxyphenyl)benzothiazoline

2-Aminothiophenol (6.3 g., 0.05 mole) and 8.3 g (0.05 mole) of 2,5-dimethoxybenzaldehyde were combined and mixed thoroughly. After a few minutes the mixture evolved heat, became cloudy, and slowly crystallized. The mixture was then warmed for a few minutes to complete the reaction. The product was then recrystallized from ethanol yielding 8.0 g (59%), mp. 96°–99°.

Anal. Calcd. for $C_{15}H_{15}NO_2S$: C, 65.93; H, 5.53; N, 5.13. Found: C, 65.97; H, 5.54; N, 5.00.

Preparation of 2-[2-(1-Carbethoxy-1-pentoxy)phenyl]-benzothiazoline

The intermediate 2-(1-carbethoxy-1-pentoxy)-benzaldehyde was prepared as follows:

To a solution of 16.8 g (0.3 mole) of potassium hydroxide in 100 ml. of ethanol was added 36.6 g (0.3 mole) of salicylaldehyde. The mixture was refluxed for 10 minutes and 70.0 g (0.31 mole) of ethyl 2-bromohexanoate was added. The mixture was refluxed for 6 hours and most of the ethanol was removed by distillation. Water was added to dissolve the precipitated salt and the product was extracted twice with ether. The ether solution was washed with 10% KOH solution and then with water, and was dried over magnesium sulfate. The ether was removed by distillation and the aldehyde was distilled, bp. 153°–154° (0.5 mm). Yield, 16.0 g (20%).

2-Aminothiophenol (6.3 g. 0.05 mole) and 13.2 g (0.05 mole) of the above prepared aldehyde were combined. The reaction was complete in a few minutes and the product was recrystallized from ethanol, wt. 14.0 g (76%), mp. 73°–74°.

Anal. Calcd. for $C_{21}H_{25}NO_3S$: C, 67.91; H, 6.78; N, 3.77. Found: C, 67.69; H, 6.74; N, 3.50.

The invention is practiced by applying to a locus, subject to attack by acarids, an acaricidal amount of a chemical of the kind described. Frequently the locus is either plant life, for example such crops as alfalfa, apples, corn, cotton, grapes, oranges, potatoes, sorghum, peanuts, etc., or animal life, including man. The chemicals may be applied alone or with a carrier, which may enhance the effectiveness of the active agent or facilitate handling, to loci to be protected against acarids, for example as dusts when admixed with or adsorbed on powdered solid carriers, such as the various mineral silicates, e.g., mica, talc, pyrophillite and clays, or as liquids or sprays when in a liquid carrier, as in solution in a suitable solvent, such as acetone, benzene or kerosene, or dispersed in a suitable nonsolvent medium, for example, water. In protecting plants (the term including plant parts) which are subject to attack by these pests, the chemicals of the present invention are preferably applied as aqueous emulsions containing a surface-active dispersing agent, which may be an anionic, nonionic or cationic surface-active agent. Such surface-active agents are well known and reference is made to U.S. Pat. No. 2,547,724 columns 3 and 4 for detailed examples of the same. The chemicals of the invention may be mixed with such surface-active dispersing agents, with or without an organic solvent as acaricidal concentrates for subsequent addition of water to make aqueous suspensions of the chemicals of the desired concentration. The chemicals of the invention may be admixed with powdered solid carriers, such a mineral silicates, together with a surface-active dispersing agent so that a wettable powder may be obtained, which may be applied directly to loci to be protected against acarids, or which may be shaken up with water to form a suspension of the chemical (and powdered solid carrier) in water for application in that form. The chemicals of the present invention may be applied to loci to be protected against acarids by the aerosol method. Solutions for the aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in a less volatile solvent and then admixing such solution with the highly volatile liquid aerosol carrier. The chemicals may be used admixed with carriers that are active of themselves, for example, other insecticides, acaricides, fungicides, or bactericides.

Practical formulations ordinarily contain from 1 to 95% active ingredient. Spray dilutions may range from a few parts per million to undiluted concentrate applied by ultra low volume techniques. The concentration of chemical per acre would vary depending upon many factors, but normally range from 0.1 to 10 pounds.

In one aspect, the invention is directed to new acaricidal compositions, comprising the described benzothiazole or benzothiazoline chemical, in acaricidal amount, in combination with a carrier therefor.

The following examples will serve to illustrate the practice of the invention in more detail.

EXAMPLE I

MITE CONTACT TEST

Cotton in the second primay leaf stage, grown in 12 ounce cups under greenhouse conditions at 70°–75° F, was used in this test. One plant (two primary leaves) in one pot was used for each replicate; two replicates were used for each chemical tested. A 1-inch diameter circle of tree tanglefoot, a sticky, non-toxic preparation, was used to confine the mites to the upper leaf surfaces. Approximately 25 adult two-spotted spider mites (*Tetranychus urticae*) were transferred to each test plant 24 hours prior to treatment.

Test compunds were prepared for spraying at 1000 ppm (parts per million) concentration by dissolving them in a small amount of acetone and adding a suitable wetting agent. Typically, 0.6 grams of chemical was dissolved (or suspended) in 10 ml of acetone, two drops of Triton x100 (trademark) wetting agent (octylphenoxy polyethoxy ethanol with 9–10 mole percent of polyethylene oxide) were added and this was suspended in 100 ml of water to make a 6000 ppm suspension. An aliquot was then further diluted with distilled water to 1000 ppm concentration of chemical.

The infested plants were sprayed with the dispersions using a small spray atomizer to thoroughly drench the foliage. The plants were returned to the greenhouse where they were held for 6 days. After this period the plants were examined for adult live mites remaining on the leaves. On an estimation basis and in comparison with the number of living mites on the check plants, the percent control was determined.

Data for the mite contact test are shown in Tables I and II.

EXAMPLE II

MITE ONE-DAY RESIDUAL TEST

Cotton in the second primary leaf stage, grown in 12 ounce cups under greenhouse conditions at 70°–75° C, was used in this test.

One plant (two primary leaves) in one pot was used for each replicate; two replicates were used for each concentration of chemical tested.

Test compounds were prepared by dissolving 50 mgs of chemical in 1 ml of acetone, adding one drop of Emulfor 719 (trademark), a commercial surface-active dispersing agent (polyoxyethylated vegetable oil) and suspended in 50 ml of water for a concentration of 1000 ppm (parts per million). Aliquots were further diluted with distilled water to the concentration tested.

The plants were sprayed with the dispersions of the chemicals, using a small spray atomizer to thoroughly drench the foliage.

One day following treatment a circle of tree tanglefoot was placed on the upper surfaces of the treated leaves and adult mites were transferred into this confinement. Counts of these mites were made immediately following transfer and again 6 days later.

Abbotts formula was used to compensate for check mortality. The adjusted percent control was obtained as follows:

$$\text{Adjusted \% Control} = \frac{\text{\% Live Mites on Check Plants} - \text{\% Live Mites on Treated Plants}}{\text{\% Live Mites on Check Plants}} \times 100$$

Data from the mite 1-day residual test are shown in Tables III and IV.

The chemicals make it possible to ameliomate phytotoxicity problems encountered with certain conventional miticides.

TABLE I

BENZOTHIAZOLES

| Name | Calculated C | Calculated H | Calculated N | Found C | Found H | Found N | m.p. ° C. | Mite Contact Test % Control at 1000 ppm |
|---|---|---|---|---|---|---|---|---|
| 2-Phenylbenzothiazole | | | | | | | 114–115 | 79 |
| 2-(1-Naphthyl)benzothiazole | 78.15 | 4.24 | 5.36 | 77.21 | 4.22 | 5.58 | 80–82 | 100 |
| 2-(2-Naphthyl)benzothiazole | 78.15 | 4.24 | 5.36 | 78.81 | 4.46 | 5.28 | 124–125 | 100 |
| 2-(o-Tolyl)benzothiazole | | | | | | | 52–55 | 96 |
| 2-(p-t-Butylphenyl)-benzothiazole | 76.38 | 6.41 | 5.24 | 76.27 | 6.33 | 5.18 | 105–107 | 100 |
| 2-(2-Chlorophenyl)-benzothiazole | 63.72 | 3.29 | 5.72 | 63.69 | 3.15 | 5.91 | 82–83 | 98 |
| 2-(4-Chlorophenyl)-benzothiazole | 63.72 | 3.29 | 5.72 | 63.29 | 3.59 | 5.73 | 112–114 | 100 |
| 2-(2-Hydroxyphenyl)-benzothiazole | | | | | | | 127–128 | 100 |
| 2-(2-Hydroxy-5-bromophenyl)benzothiazole | 51.00 | 2.63 | 4.58 | 51.02 | 2.59 | 4.97 | 164–165 | 100 |
| 2-(2-Hydroxy-3-methylphenyl)benzothiazole | 69.70 | 4.60 | 5.81 | 69.51 | 4.29 | 5.58 | 138–139 | 100 |
| 2-(2-Hydroxy-4-methylphenyl)benzothiazole | 69.70 | 4.60 | 5.81 | 69.34 | 4.81 | 5.56 | 142–143 | 100 |
| 2-(2-Hydroxy-5-methylphenyl)benzothiazole | 69.70 | 4.60 | 5.81 | 69.23 | 4.62 | 5.82 | 128–129 | 98 |
| 2-(5-t-Butyl-2-hydroxyphenyl)benzothiazole | | | | | | | 102–103 | 100 |
| 2-(3-Methoxyphenyl)-benzothiazole | 69.70 | 4.60 | 5.81 | 69.50 | 4.64 | 6.03 | 85–87 | 95 |
| 2-(4-Methoxyphenyl)-benzothiazole | 69.70 | 4.60 | 5.81 | 69.44 | 4.71 | 5.04 | 112–113 | 100 |
| 2-(2-Ethoxyphenyl)-benzothiazole | 70.58 | 5.13 | 5.49 | 70.36 | 5.06 | 5.53 | 74–76 | 100 |
| 2-[2-(1-Butoxy)phenyl]-benzothiazole | 72.07 | 6.05 | 4.94 | 72.33 | 6.04 | 4.85 | 94–96 | 95 |
| 2-[2-(2-Octyloxy)phenyl]- | | | | | | | | |

TABLE I-continued
BENZOTHIAZOLES

| Name | Calculated C | Calculated H | Calculated N | Found C | Found H | Found N | m.p. °C. | Mite Contact Test % Control at 1000 ppm |
|---|---|---|---|---|---|---|---|---|
| benzothiazole | 74.31 | 7.42 | 4.13 | 74.71 | 7.61 | 4.14 | Liquid | 100 |
| 2-(2-Cyclopentoxyphenyl)-benzothiazole | 73.20 | 5.80 | 4.74 | 73.84 | 6.10 | 4.77 | Liquid | 100 |
| 2-(2,4-Dimethoxyphenyl)-benzothiazole | 66.41 | 4.83 | 5.16 | 66.10 | 4.94 | 4.93 | 139–140 | 75 |
| 2-(2,5-Dimethoxyphenyl)-benzothiazole | 66.41 | 4.83 | 5.16 | 66.16 | 5.17 | 5.05 | 108–110 | 100 |
| 2-(4-Ethoxy-3-methoxyphenyl)benzothiazole | 67.36 | 5.30 | 4.91 | 67.08 | 5.90 | 4.84 | 146–148 | 90 |
| 2-(2-Ethoxy-3-methoxyphenyl)benzothiazole | 67.36 | 5.30 | 4.91 | 66.55 | 5.33 | 4.75 | 88–90 | 96 |
| 2-(2-Benzothiazolyl)-phenyl acetate | 66.91 | 4.12 | 5.20 | 67.91 | 3.90 | 5.66 | 53–55 | 100 |
| 2-(2-Benzothiazolyl)-phenyl propionate | 67.84 | 4.63 | 4.94 | 67.98 | 4.55 | 5.06 | 72–74 | 100 |
| 2-(2-Benzothiazolyl)-phenyl butyrate | 68.68 | 5.09 | 4.71 | 68.62 | 5.04 | 4.81 | 50–52 | 100 |
| 2-[2-(1-Carbo-2-propoxymethoxy)phenyl]-benzothiazole | 66.05 | 5.23 | 4.28 | 65.71 | 5.13 | 4.47 | Low-melting solid | 100 |

TABLE II
BENZOTHIAZOLINES

| Name | Calculated C | Calculated H | Calculated N | Found C | Found H | Found N | m.p. °C. | Mite Contact Test % Control at 1000 ppm |
|---|---|---|---|---|---|---|---|---|
| 2-Phenylbenzothiazoline | 73.23 | 5.20 | 6.57 | 73.08 | 5.33 | 6.50 | 78–80 | 95 |
| 2-(1-Naphthyl)-benzothiazoline | 77.55 | 4.98 | 5.32 | 77.35 | 4.97 | 5.44 | 132–134 | 100 |
| 2-(2-Naphthyl)-benzothiazoline | 77.55 | 4.98 | 5.32 | 77.30 | 4.95 | 5.52 | 118–120 | 100 |
| 2-(p-Tolyl)benzothiazoline | 73.99 | 5.77 | 6.16 | 73.76 | 5.66 | 6.28 | 84–86 | 100 |
| 2-(4-Ethylphenyl)benzothiazoline | 74.67 | 6.27 | 5.80 | 74.03 | 5.43 | 5.74 | Liquid | 100 |
| 2-(4-Isopropylphenyl)-benzothiazoline | 75.27 | 6.71 | 5.49 | 75.43 | 6.39 | 5.64 | 43–45 | 100 |
| 2-[4-(1-Butyl)phenyl]-benzothiazoline | 75.81 | 7.11 | 5.20 | 75.72 | 6.90 | 5.03 | Low melting solid | 100 |
| 2-(p-t-Butylphenyl)benzothiazoline | 75.81 | 7.11 | 5.20 | 76.31 | 7.23 | 5.24 | 92–94 | 100 |
| 2-[4-(2-Amyl)phenyl]-benzothiazoline | 76.30 | 7.47 | 4.94 | 76.34 | 7.45 | 4.59 | Liquid | 100 |
| 2-(2,4-Dimethylphenyl)-benzothiazoline | 74.67 | 6.27 | 5.80 | 74.63 | 6.11 | 5.89 | Low melting solid | 100 |
| 2-(2,5-Dimethylphenyl)-benzothiazoline | 74.67 | 6.27 | 5.80 | 74.70 | 6.21 | 5.81 | 76–78 | 100 |
| 2-(4-Chlorophenyl)-benzothiazoline | 63.11 | 4.08 | 5.66 | 62.78 | 4.01 | 5.65 | 85–87 | 100 |
| 2-(2-Chlorophenyl)-benzothiazoline | 63.11 | 4.08 | 5.66 | 63.01 | 5.05 | 5.62 | 85–86 | 90 |
| 2-(4-Bromophenyl)-benzothiazoline | 53.47 | 3.45 | 4.80 | 53.37 | 3.56 | 4.74 | 96–98 | 100 |
| 2-(2,4-Dichlorophenyl)-benzothiazoline | 55.37 | 3.23 | 4.97 | 55.13 | 3.27 | 5.15 | 90–92 | 100 |
| 2-(3,4-Dichlorophenyl)-benzothiazoline | 55.37 | 3.23 | 4.97 | 55.19 | 3.18 | 5.12 | 97–99 | 100 |
| 2-(2-Hydroxyphenyl)-benzothiazoline | | | | | | | 136–137 | 100 |
| 2-(3-Hydroxyphenyl)-benzothiazoline | 68.11 | 4.84 | 6.11 | 68.81 | 4.47 | 6.23 | 150–155 | 80 |
| 2-(2-Methoxyphenyl)-benzothiazoline | 69.12 | 5.39 | 5.76 | 69.27 | 5.36 | 5.67 | 89–92 | 100 |
| 2-(2-ethoxyphenyl)-benzothiazoline | 70.02 | 5.88 | 5.44 | 69.75 | 5.62 | 5.47 | 72–74 | 95 |
| 2-[2-(1-Propoxy)phenyl]-benzothiazoline | 70.83 | 6.32 | 5.16 | 70.78 | 5.59 | 5.08 | Liquid | 100 |
| 2-[2-(2-Propoxy)phenyl]-benzothiazoline | 71.36 | 5.61 | 5.20 | 71.49 | 5.70 | 5.43 | Low melting solid | 100 |
| 2-[2-(1-Butoxy)phenyl]-benzothiazoline | 71.56 | 6.71 | 4.91 | 71.35 | 6.18 | 5.10 | Low melting solid | 100 |
| 2-[2-(2-Butoxy)phenyl]-benzothiazoline | 71.56 | 6.71 | 4.91 | 71.28 | 6.45 | 4.94 | Liquid | 100 |
| 2-[2-(1-Pentoxy)phenyl]-benzothiazoline | 72.22 | 7.07 | 4.68 | 71.65 | 6.67 | 4.57 | Low melting solid | 100 |
| 2-[2-(1-Octyloxy)phenyl]-benzothiazoline | 73.87 | 7.97 | 4.10 | 73.96 | 7.64 | 4.18 | Low melting solid | 100 |
| 2-[2-(2-Octyloxy)phenyl]-benzothiazoline | 73.87 | 7.97 | 4.10 | 73.89 | 7.98 | 3.91 | Liquid | 100 |

TABLE II-continued

BENZOTHIAZOLINES

| Name | Calculated | | | Found | | | m.p. °C. | Mite Contact Test % Control at 1000 ppm |
|---|---|---|---|---|---|---|---|---|
| | C | H | N | C | H | N | | |
| 2-[2-(1-Decoxy)phenyl]-benzothiazoline | 74.76 | 8.46 | 3.79 | 74.74 | 8.12 | 3.90 | Low melting solid | 100 |
| 2-[2-(1-Dodecoxy)phenyl]-benzothiazoline | 75.53 | 8.87 | 3.52 | 75.56 | 8.66 | 3.82 | Liquid | 100 |
| 2-[2-(1-Tetradecoxy)-phenyl]benzo-thiazoline | 76.20 | 9.24 | 3.29 | 76.09 | 9.22 | 3.17 | Liquid | 90 |
| 2-[2-(2,2-Dichlorocyclo-propylmethoxy)phenyl]-benzothiazoline | 58.01 | 4.29 | 3.98 | 58.18 | 4.25 | 4.27 | Liquid | 98 |
| 2-[2-(2,2-Dichloro-1-methylcyclopropyl-methoxy)phenyl]-benzothiazoline | 59.07 | 4.68 | 3.83 | 58.45 | 4.66 | 4.08 | Liquid | 100 |
| 2-[2-(1-Cyclohexyl-methoxy)phenyl]-benzothiazoline | | | | | | | Liquid | 100 |
| 2-(2-Cyclopentoxy-phenyl)benzo-thiazoline | 72.71 | 6.44 | 4.71 | 72.02 | 6.25 | 4.89 | Liquid | 100 |
| 2-(2-Cyclohexoxyphenyl)-benzothiazoline | | | | | | | Liquid | 98 |
| 2-(2-Cycloheptoxyphenyl)-benzothiazoline | 73.82 | 7.12 | 4.30 | 74.11 | 7.10 | 4.44 | Liquid | 100 |
| 2-(3-Ethoxyphenyl)benzo-thiazoline | 70.02 | 5.88 | 5.44 | 70.06 | 5.64 | 5.17 | Liquid | 100 |
| 2-[3-(1-Butoxy)phenyl]-benzothiazoline | 71.56 | 6.71 | 4.91 | 70.94 | 6.24 | 5.28 | Liquid | 100 |
| 2-[3-(1-Pentoxy)phenyl]-benzothiazoline | 72.22 | 7.07 | 4.68 | 71.37 | 6.76 | 5.06 | Liquid | 100 |
| 2-(4-Methoxyphenyl)-benzothiazoline | 69.12 | 5.39 | 5.76 | 68.93 | 5.36 | 6.06 | 70–72 | 90 |
| 2(4-Ethoxyphenyl)-benzothiazoline | 70.02 | 5.88 | 5.44 | 69.95 | 5.66 | 5.75 | 84–89 | 100 |
| 2[4-(1-Propoxy)phenyl]-benzothiazoline | 70.83 | 6.32 | 5.16 | 70.85 | 6.16 | 5.38 | 72–74 | 90 |
| 2-[4-(1-Butoxy)phenyl]-benzothiazoline | 71.56 | 6.71 | 4.91 | 71.75 | 6.50 | 5.16 | 70–73 | 100 |
| 2-[4-(1-Pentoxy)phenyl]-benzothiazoline | 72.22 | 7.07 | 4.68 | 72.05 | 7.01 | 4.67 | 57–58 | 95 |
| 2-[4-(1-Hexyloxy)phenyl]-benzothiazoline | 72.82 | 7.40 | 4.47 | 73.57 | 7.21 | 4.46 | 55–56 | 100 |
| 2-[4-(1-Octyloxy)phenyl]-benzothiazoline | 73.87 | 7.97 | 4.10 | 74.32 | 8.14 | 4.04 | 51–52 | 90 |
| 2-[4-(2,2-Dichlorocyclo-propylmethoxy)phenyl]-benzothiazoline | 58.01 | 4.29 | 3.98 | 58.63 | 4.18 | 4.04 | 96–97 | 80 |
| 2-[4-(2,2-Dichloro-1-methylcyclopropyl-methoxy)phenyl]-benzothiazoline | 59.07 | 4.68 | 3.83 | 59.20 | 4.74 | 3.91 | 107–108 | 90 |
| 2-(4-Cyclopentoxyphenyl)-benzothiazoline | 72.71 | 6.44 | 4.71 | 72.80 | 6.40 | 4.42 | 78–79 | 100 |
| 2-(4-Cyclohexoxyphenyl)-benzothiazoline | 73.29 | 6.80 | 4.50 | 73.31 | 6.81 | 4.31 | 74–75 | 96 |
| 2-[2-(1-Carbethoxymethoxy)-phenyl]benzothiazo-line | 64.73 | 5.43 | 4.44 | 65.00 | 5.64 | 4.31 | 107–108 | 80 |
| 2-[2-(1-Carbethoxypropoxy)-phenyl]benzo-thiazoline | 66.46 | 6.16 | 4.08 | 65.62 | 5.89 | 4.27 | Liquid | 100 |
| 2-(2,3-Dimethoxyphenyl)-benzothiazoline | 65.93 | 5.53 | 5.13 | 65.80 | 5.63 | 5.00 | 90–95 | 100 |
| 2-(2,5-Dimethoxyphenyl)-benzothiazoline | 65.93 | 5.53 | 5.13 | 65.97 | 5.54 | 5.00 | 96–99 | 90 |
| 2-(3,4-Dimethoxyphenyl)-benzothiazoline | 65.93 | 5.53 | 5.13 | 66.50 | 5.07 | 5.20 | 132–134 | 99 |
| 2-(4-Ethoxy-3-methoxy-phenyl)benzo-thiazoline | 66.89 | 5.96 | 4.87 | 66.87 | 6.01 | 4.86 | 106–108 | 95 |
| 2-(2-Ethoxy-3-methoxy-phenyl)benzo-thiazoline | 66.89 | 5.96 | 4.87 | 66.48 | 5.90 | 5.06 | 75–77 | 100 |
| 2-[2-(Carbomethoxy-methoxy)phenyl]benzo-thiazoline | 63.78 | 5.02 | 4.65 | 64.47 | 5.65 | 4.36 | 103–104 | 100 |
| 2-[2-(1-Carbomethoxy-ethoxy)phenyl]-benzothiazoline | 64.75 | 5.43 | 4.44 | 64.48 | 5.29 | 4.45 | 83–85 | 100 |
| 2-[2-(1-Carbomethoxy-propoxy)phenyl]-benzothiazoline | 65.64 | 5.81 | 4.25 | 64.98 | 5.81 | 4.51 | Liquid | 100 |
| 2-[2-(1-Carbethoxymethoxy)-phenyl]benzo-thiazoline | 64.75 | 5.43 | 4.44 | 65.00 | 5.64 | 4.31 | 107–108 | 80 |
| 2-[2-(1-Carbethoxyethoxy)- | | | | | | | | |

TABLE II-continued

BENZOTHIAZOLINES

| Name | Calculated C | H | N | Found C | H | N | m.p. °C. | Mite Contact Test % Control at 1000 ppm |
|---|---|---|---|---|---|---|---|---|
| phenyl]benzothiazoline | 65.64 | 5.81 | 4.25 | 65.84 | 5.94 | 4.08 | 78–79 | 100 |
| 2-[2-(1-Carbethoxypropoxy)phenyl]benzothiazoline | 66.46 | 6.16 | 4.08 | 65.62 | 5.97 | 4.26 | Liquid | 100 |
| 2-[2-(1-Carbethoxybutoxy)phenyl]benzothiazoline | 67.21 | 6.49 | 3.92 | 67.45 | 6.57 | 4.00 | 75–76 | 100 |
| 2-[2-(1-Carbethoxypentoxy)phenyl]benzothiazoline | 67.91 | 6.78 | 3.77 | 67.69 | 6.74 | 3.50 | 73–74 | 95 |
| 2-[2-(2-Carbethoxy-2-propoxy)phenyl]benzothiazoline | 66.46 | 6.16 | 4.08 | 65.85 | 6.14 | 3.86 | 78–80 | 100 |
| 2-[2-(1-Carbo-2-propoxypropoxy)phenyl]benzothiazoline | | | | | | | Liquid | 90 |
| 2-[2-(1-Carbo-2-propoxypentoxy)phenyl]benzothiazoline | | | | | | | Liquid | 90 |
| 2-[2-(1-Carboxycyclohexoxypropoxy)phenyl]benzothiazoline | | | | | | | Liquid | 90 |
| 2-[4-(1-Carbethoxypropoxy)phenyl]benzothiazole | 66.46 | 6.16 | 4.08 | 66.29 | 5.55 | 4.33 | Liquid | 70 |

TABLE III

BENZOTHIAZOLES

| | Mite 1-day Residual Test % Control at | |
|---|---|---|
| | 500 ppm | 100 ppm |
| 2-(1-Naphthyl)benzothiazole | 100 | 94 |
| 2-(p-t-Butylphenyl)benzothiazole | 100 | 100 |
| 2-(4-Chlorophenyl)benzothiazole | 100 | 46 |
| 2-(2-Hydroxy-5-bromophenyl)benzothiazole | 98 | 78 |
| 2-(2-Hydroxy-3-methylphenyl)benzothiazole | 84 | 48 |
| 2-(2-Hydroxy-4-methylphenyl)benzothiazole | 75 | 47 |
| 2-(2-Hydroxy-5-methylphenyl)benzothiazole | 78 | 25 |
| 2-(5-t-Butyl-2-hydroxyphenyl)benzothiazole | 100 | 94 |
| 2-(2-Ethoxyphenyl)benzothiazole | 98 | 41 |
| 2-[2-(1-Butoxy)phenyl]benzothiazole | 96 | 93 |
| 2-[2-(2-Octyloxy)phenyl]benzothiazole | 100 | 100 |
| 2-(2-Cyclopentoxyphenyl)benzothiazole | 100 | 93 |
| 2-(2,5-Dimethoxyphenyl)benzothiazole | 96 | 76 |
| 2-(2-Ethoxy-3-methoxyphenyl)benzothiazole | 94 | 51 |
| 2-[2-(1-Carbo-2-propoxymethoxy)phenyl]benzothiazole | 90 | 63 |

TABLE IV

BENZOTHIAZOLINES

| | Mite 1-day Residual Test Control at | |
|---|---|---|
| | 500 ppm | 100 ppm |
| 2-(1-Naphthyl)benzothiazoline | 100 | 100 |
| 2-(p-Tolyl)benzothiazoline | 100 | 0 |
| 2-(4-Ethylphenyl)benzothiazoline | 100 | 54 |
| 2-(4-Isopropylphenyl)benzothiazoline | 100 | 61 |
| 2-[4-(1-Butyl)phenyl]benzothiazoline | 95 | 57 |
| 2-(p-t-Butylphenyl)benzothiazoline | 100 | 99 |
| 2-[4-(2-Amyl)phenyl]benzothiazoline | 93 | 72 |
| 2-(4-Chlorophenyl)benzothiazoline | 100 | 98 |
| 2-(4-Bromophenyl)benzothiazoline | 100 | 92 |
| 2-(2,4-Dichlorophenyl)benzothiazoline | 100 | 5 |
| 2-(3,4-Dichlorophenyl)benzothiazoline | 100 | 55 |
| 2-(2-Methoxyphenyl)benzothiazoline | 75 | 22 |
| 2-(2-Ethoxyphenyl)benzothiazoline | 91 | 34 |
| 2-[2-(1-Propoxy)phenyl]benzothiazoline | 100 | 99 |
| 2-[2-(2-Propoxy)phenyl]benzothiazoline | 100 | 88 |
| 2-[2-(1-Butoxy)phenyl]benzothiazoline | 100 | 44 |
| 2-[2-(2-Butoxy)phenyl]benzothiazoline | 100 | 62 |
| 2-[2-(1-Pentoxy)phenyl]benzothiazoline | 97 | 23 |
| 2-[2-(1-Octyloxy)phenyl]benzothiazoline | 85 | 39 |
| 2-[2-(2-Octyloxy)phenyl]benzothiazoline | 100 | 100 |
| 2-[2-(1-Decoxy)phenyl]benzothiazoline | 91 | 79 |
| 2-[2-(1-Dodecoxy)phenyl]benzothiazoline | 76 | 69 |
| 2-[2-(1-Tetradecoxy)phenyl]benzothiazoline | 92 | 78 |
| 2-[2-(1-Cyclohexylmethoxy)phenyl]benzothiazoline | 100 | 88 |
| 2-(2-Cyclopentoxyphenyl)benzothiazoline | 100 | 100 |
| 2-(2-Cyclohexoxyphenyl)benzothiazoline | 97 | 98 |
| 2-(2-Cycloheptoxyphenyl)benzothiazoline | 72 | 29 |

TABLE IV-continued
BENZOTHIAZOLINES

| | Mite 1-day Residual Test Control at | |
|---|---|---|
| | 500 ppm | 100 ppm |
| 2-(3-Ethoxyphenyl)benzothiazoline | 78 | 68 |
| 2-[3-(1-Butoxy)phenyl]benzothiazoline | 100 | 76 |
| 2-[3-(1-Pentoxy)phenyl]benzothiazoline | 99 | 22 |
| 2-(4-Methoxyphenyl)benzothiazoline | 77 | 37 |
| 2-[4-(1-Propoxy)phenyl]benzothiazoline | 77 | 58 |
| 2-[4-(1-Butoxy)phenyl]benzothiazoline | 93 | 70 |
| 2-[2-(1-Carbethoxypropoxy)phenyl]benzothiazoline | 98 | 80 |
| 2-(2,5-Dimethoxyphenyl)benzothiazoline | 100 | 70 |
| 2-[2-(1-Carbethoxyethoxy)phenyl]benzothiazoline | 81 | 21 |
| 2-[2-(1-Carbethoxypropoxy)phenyl]benzothiazoline | 98 | 80 |
| 2-[2-(1-Carbethoxybutoxy)phenyl]benzothiazoline | 96 | 68 |
| 2-[2-(1-Carbethoxypentoxy)phenyl]benzothiazoline | 100 | 68 |
| 2-[2-(2-Carbethoxy-2-propoxy)phenyl]benzothiazoline | 97 | 74 |
| 2-[2-(1-Carbo-2-propoxypentoxy)phenyl]benzothiazoline | 70 | 30 |

We claim:
1. A method of controlling acarids comprising applying, to a locus subject to attack by acarids, an acaricidal amount of benzothiazoline of the formula

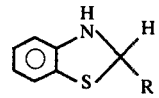

where R is 1-naphthyl or 2-naphthyl.
2. The method of claim 1 in which the said locus is plant life.
3. The method of claim 1 in which the said acarids are mites.
4. The method of claim 1 in which the said locus is plant life and the said acarids are mites.
5. The method of claim 4 in which the said benzothiazoline is 2-(1-naphthyl)benzothiazoline.
6. The method of claim 4 in which the said benzothiazoline is 2-(2-naphthyl) benzothiazoline.

* * * * *